(12) United States Patent
Abe et al.

(10) Patent No.: US 8,647,274 B2
(45) Date of Patent: Feb. 11, 2014

(54) ULTRASOUND DIAGNOSIS APPARATUS, IMAGE PROCESSING APPARATUS, AND IMAGE PROCESSING METHOD

(75) Inventors: Yasuhiko Abe, Otawara (JP); Tetsuya Kawagishi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/409,713

(22) Filed: Mar. 1, 2012

(65) Prior Publication Data

US 2012/0165674 A1 Jun. 28, 2012

Related U.S. Application Data

(63) Continuation of application No. PCT/JP2011/006987, filed on Aug. 31, 2011.

(30) Foreign Application Priority Data

Sep. 8, 2010 (JP) .................................. 2010-201241

(51) Int. Cl.
*A61B 8/14* (2006.01)

(52) U.S. Cl.
USPC ........... 600/437; 600/439; 600/407; 600/459; 378/8

(58) Field of Classification Search
USPC ..................... 600/407, 437, 443, 459; 378/8
See application file for complete search history.

(56) References Cited

U.S. PATENT DOCUMENTS

| 2003/0153823 A1* | 8/2003 | Geiser et al. ................... 600/407 |
| 2006/0224203 A1 | 10/2006 | Hettrick et al. |
| 2007/0167801 A1* | 7/2007 | Webler et al. ................... 600/459 |
| 2008/0170654 A1* | 7/2008 | Tkaczyk et al. ................... 378/8 |
| 2010/0228127 A1 | 9/2010 | Allain et al. |

FOREIGN PATENT DOCUMENTS

| JP | 2008-535555 | 9/2008 |
| JP | 2008-301920 | 12/2008 |
| JP | 2010-500082 | 1/2010 |
| JP | 2010-115372 | 5/2010 |

OTHER PUBLICATIONS

International Search Report issued Nov. 8, 2011, in PCT/JP2011/069787 (submitting English translation only).

(Continued)

*Primary Examiner* — Baisakhi Roy
(74) *Attorney, Agent, or Firm* — Oblon, Spivak, McClelland, Maier & Neustadt, L.L.P.

(57) ABSTRACT

According to one embodiment, an ultrasound diagnosis apparatus includes a motion information generating unit and a control unit. The motion information generating unit generates first motion information on cardiac wall motion of at least one of a left ventricle and a left atrium and second motion information on cardiac wall motion of at least one of a right ventricle and a right atrium, on the basis of a first volume data group and a second volume data group; generates first correction information and second correction information by correcting the first motion information and the second motion information such that the first motion information and the second motion information are substantially synchronized with each other, and generates a motion information image in which the first correction information and the second correction information are arranged along the time axis. The control unit controls to display the motion image information.

14 Claims, 9 Drawing Sheets

(56) References Cited

OTHER PUBLICATIONS

International Search Report issued on Nov. 8, 2011 for PCT/JP11/069787 filed Aug. 31, 2011 with English Translation of categories.
International Written Opinion issued on Nov. 8, 2011 for PCT/JP11/069787 filed Aug. 31, 2011.
Tomoyuki Takeguchi, et al.; "Practical considerations for a method of rapid cardiac function analysis based on three-dimensional speckle tracking in a three-dimensional diagnostic ultrasound system"; Journal of Medical Ultrasonics, vol. 37, No. 2, 41-49, 2010.
Hidekazu Tanaka MD, et al.; "Usefulness of Three-Dimensional Speckle Tracking Strain to Quantify Dyssynchrony and the Site of Latest Mechanical Activation"; The American Journal of Cardiology, vol. 105, Issue 2, 235-454, 2010.
Chinese Office Action dated Nov. 4, 2013 in application No. 201180002090.2.

* cited by examiner

FIG.4A

| EDV (mL) |
| --- |
| ESV (mL) |
| EF (%) |
| MYOCARDIAL VOLUME (mL) |
| MYOCARDIAL MASS (g) |
| MASS-INDEX (g/m²) |
| TEMPORAL CHANGE CURVE OF INTRACAVITY VOLUME |

FIG.4B

| REGIONAL MYOCARDIAL STRAIN (%) |
| --- |
| REGIONAL MYOCARDIAL STRAIN RATE (1/s) |
| REGIONAL MYOCARDIAL DISPLACEMENT (cm) |
| REGIONAL MYOCARDIAL VELOCITY (cm/s) |

FIG.5
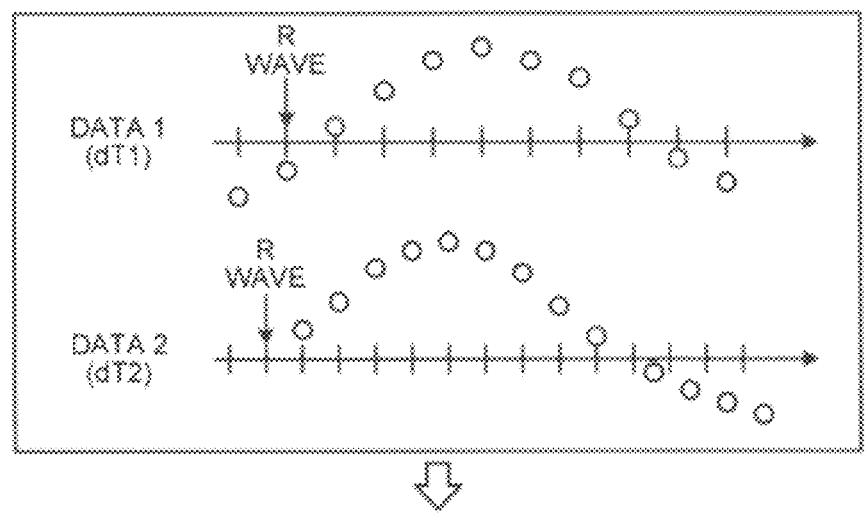
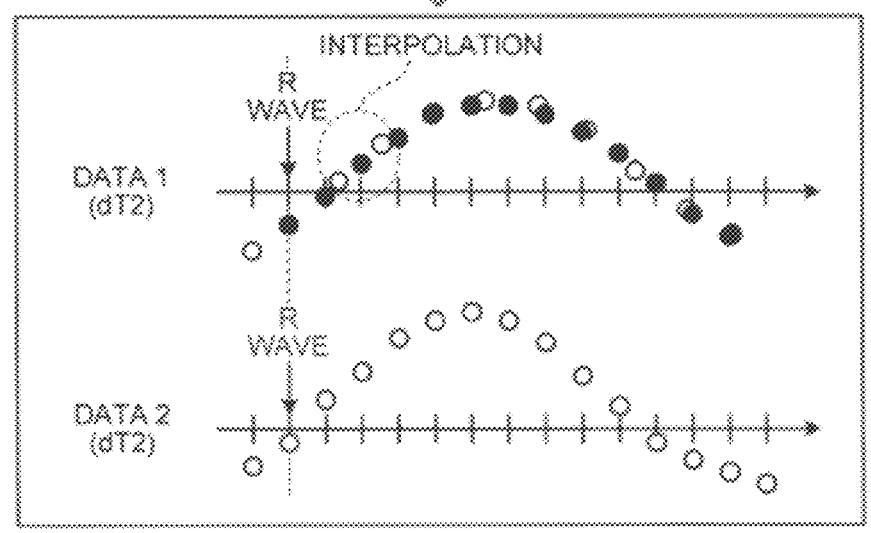
FIG.6
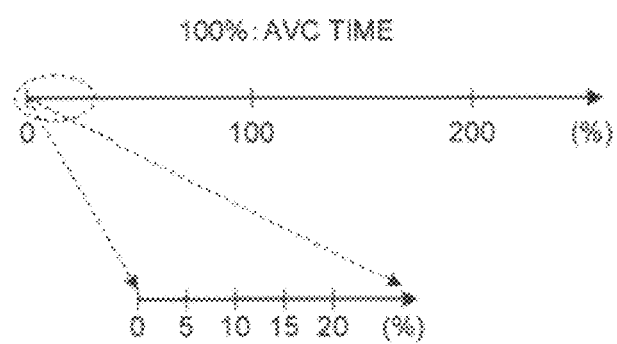

ULTRASOUND DIAGNOSIS APPARATUS, IMAGE PROCESSING APPARATUS, AND IMAGE PROCESSING METHOD

CROSS-REFERENCE TO RELATED APPLICATIONS

This application is a continuation of PCT international application Ser. No. PCT/JP2011/069787 filed on Aug. 31, 2011 which designates the United States, and which claims the benefit of priority from Japanese Patent Application No. 2010-201241, filed on Sep. 8, 2010; the entire contents of which are incorporated herein by reference.

FIELD

Embodiments described herein relate generally to an ultrasound diagnosis apparatus, an image processing apparatus, and an image processing method.

BACKGROUND

Objective and quantitative evaluation of functions of body tissue is important in diagnosing diseases of the body tissue. For example, in diagnosis of cardiac disease, a quantitative evaluation method has been attempted, in which cardiac wall motion is quantitatively evaluated by using echocardiography.

In recent years, a Cardiac Resynchronization Therapy (CRT) for performing biventricular pacing on a patient with significant heart failure has attracted attention, and it becomes important to quantitatively evaluate cardiac wall motion by using echocardiography in order to determine the application of CRT in advance or to evaluate the effect of the therapy.

CRT is a therapy that can improve cardiac wall motion dyssynchrony, which generally occurs in a patient with significant heart failure, and that provides significant improvement in symptoms in a patient who can benefit from CRT (Responder). On the other hand, it is known that approximately 30 percent of patients with heart failure receive little or no benefit from CRT (Non Responder) as of 2005. "Non Responder" indicates a patient who has heart failure other than the dyssynchrony. Conventionally, the application of CRT is determined on the basis of a QRS duration on an electrocardiogram and a left ventricular Ejection Fraction (EF). For example, a patient with the QRS duration longer than "130 milliseconds" on the electrocardiogram and the left ventricular ejection fraction less than or equal to 35% is determined as a subject to whom CRT is applicable. However, with the above criteria, a patient who has heart failure other than the dyssynchrony may be determined as a subject to whom CRT is applicable, resulting in "Non Responder".

Therefore, there has been an attempt to extract only the dyssynchrony through a quantitative evaluation method using echocardiography. Examples of the quantitative evaluation method using echocardiography include a method using speckle tracking, in which points set on a myocardium in an ultrasound image are tracked on the basis of a speckle pattern that is specific to the ultrasound image. For example, the heart of a patient is three-dimensionally scanned in a chronological order to collect volume data and the volume data is analyzed by the speckle tracking, so that it becomes possible to three-dimensionally and quantitatively evaluate the wall motion of each of the left ventricle, the right ventricle, the left atrium, and the right atrium.

Meanwhile, factors for determining whether to apply CRT or not include the degree of atrioventricular wall motion synchrony (between the left atrium and the left ventricle) or interventricular wall motion synchrony (between the right ventricle and the left ventricle), in addition to the degree of left ventricular wall motion synchrony. That is, the determination on whether to apply CRT or not depends on the degree of dyssynchrony of these factors.

However, the conventional technology described above is made to separately analyze the functions of the four chambers of a heart, and in particular, to three-dimensionally evaluate the dyssynchrony of the cardiac wall motion in the left ventricle. That is, with the above-described conventional technology, it is impossible to three-dimensionally analyze a difference in the interventricular wall motion synchrony, the interatrial wall motion synchrony, and the atrioventricular wall motion synchrony.

BRIEF DESCRIPTION OF DRAWINGS

FIG. 4A is a diagram (1) for explaining a concrete example of cardiac wall motion information generated by the motion information generating unit.

FIG. 4B is a diagram (2) for explaining a concrete example of the cardiac wall motion information generated by the motion information generating unit.

FIG. 5 is a diagram for explaining a first interpolation method performed by the motion information generating unit.

FIG. 6 is a diagram for explaining a second interpolation method performed by the motion information generating unit.

DETAILED DESCRIPTION

According to one embodiment, an ultrasound diagnosis apparatus includes a motion information generating unit and a display controlling unit. The motion information generating unit generates first motion information on cardiac wall motion of at least one of a left ventricle and a left atrium and second motion information on cardiac wall motion of at least one of a right ventricle and a right atrium, each of the first motion information and the second motion information being temporal change information that is made up of a plurality of measured values along a time axis and that indicates temporal change in cardiac wall motion, on the basis of a first volume data group including a region related to a left side of a heart of a subject and a second volume data group including a region related to a right side of the heart, each of the first volume data group and the second volume data group being obtained from volume data that is generated by three-dimensionally scanning the heart of the subject with an ultrasound wave for a duration of one or more heartbeats. And the motion information generating unit generates first correction information and second correction information by correcting the first motion information and the second motion information that are displaying objects such that the first motion information and the second motion information are substantially synchronized with each other on the basis of a cardiac phase. And the motion information generating unit generates a motion information image in which the first correction information and the second correction information are arranged along the time axis such that time phases of the first correction information and the second correction information are aligned on the basis of a predetermined cardiac phase. The display controlling unit that controls so that the motion information image is displayed on a predetermined display unit. Embodiments of an ultrasound diagnosis apparatus will be explained in detail below with reference to the accompanying drawings.

Embodiment

Figure 1:
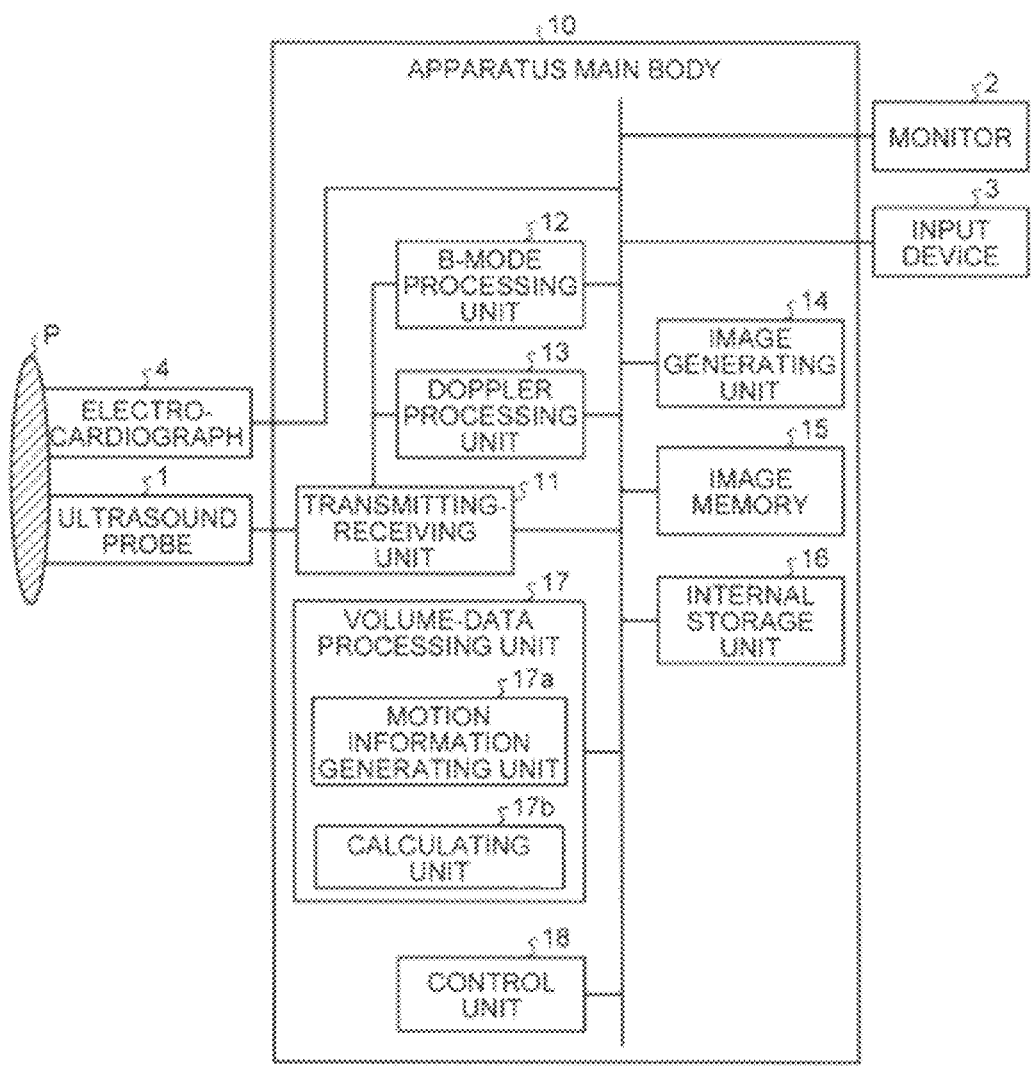
FIG. 1 is a diagram for explaining a configuration of an ultrasound diagnosis apparatus according to an embodiment.

First, a configuration of an ultrasound diagnosis apparatus according to an embodiment will be explained. FIG. 1 is a diagram for explaining the configuration of the ultrasound diagnosis apparatus according to the embodiment. As illustrated in FIG. 1, the ultrasound diagnosis apparatus according to the embodiment includes an ultrasound probe 1, a monitor 2, an input device 3, an electrocardiograph 4, and an apparatus main body 10.

The ultrasound probe 1 is an external ultrasound probe that is detachably connected to the apparatus main body 10. The ultrasound probe 1 includes a plurality of piezoelectric transducers. The piezoelectric transducers generate ultrasound waves on the basis of a drive signal provided from a transmitting-receiving unit 11 included in the apparatus main body 10, which will be explained below. The ultrasound probe 1 receives a reflected wave from a subject P and converts the reflected wave to an electrical signal. The ultrasound probe 1 also includes a matching layer arranged on the piezoelectric transducers; and a backing material that prevents ultrasound waves from propagating backward from the piezoelectric transducers.

When the ultrasound probe 1 transmits ultrasound waves to the subject P, the transmitted ultrasound waves are sequentially reflected from acoustic-impedance discontinuity surfaces of the body tissue of the subject P, and the piezoelectric transducers of the ultrasound probe 1 receive the reflected waves as reflected wave signals. The amplitude of the received reflected wave signals depends on a difference in the acoustic impedance of the discontinuity surfaces where the ultrasound waves are reflected. When the transmitted ultrasound pulses are reflected from a moving bloodstream, a moving surface of a cardiac wall, or the like, the frequencies of the reflected wave signals are shifted due to the Doppler effect in accordance with the velocity component in the ultrasound wave transmission direction in the moving body.

Meanwhile, the ultrasound probe 1 according to the embodiment is an ultrasound probe that can scan the subject P two-dimensionally as well as can scan the subject P three-dimensionally by sector scanning. Specifically, the ultrasound probe 1 according to the embodiment is an external mechanical scanning probe that scans the subject P three-dimensionally by oscillating the ultrasound transducers at a predetermined angle (swing angle).

The present embodiment is also applicable even when the ultrasound probe 1 is a two-dimensional ultrasound probe that has a plurality of ultrasound transducers arranged in a matrix form to enable three-dimensional ultrasound scanning of the subject P. The two-dimensional ultrasound probe can scan the subject P two-dimensionally by converging ultrasound waves and transmitting the converged ultrasound waves.

The input device 3 includes a mouse, a keyboard, a button, a panel switch, a touch command screen, a foot switch, a trackball, and the like, receives various setting requests from an operator of the ultrasound diagnosis apparatus, and transfers the received various setting requests to the apparatus main body 10.

For example, the input device 3 according to the embodiment receives, from an operator, designation of a type of cardiac wall motion information that is generated from volume data or designation of an output form of the generated information. The contents of various types of designation received by the input device 3 according to the embodiment will be described below.

The monitor 2 displays a Graphical User Interface (GUI) that is used by an operator of the ultrasound diagnosis apparatus to input various setting requests by using the input device 3, and displays an ultrasound image generated by the apparatus main body 10.

The electrocardiograph 4 is connected to the apparatus main body 10 and acquires an Electrocardiogram (ECG) of the subject P who is subjected to the ultrasound scanning. The electrocardiograph 4 transmits the acquired electrocardiogram to the apparatus main body 10.

The apparatus main body 10 is an apparatus that generates an ultrasound image on the basis of the reflected waves received by the ultrasound probe 1. Specifically, the apparatus main body 10 according to the embodiment is an apparatus that can generate a three-dimensional ultrasound image (volume data) based on three-dimensional reflected wave data that is received by the ultrasound probe 1. The apparatus main body 10 includes, as illustrated in FIG. 1, the transmitting-receiving unit 11, a B-mode processing unit 12, a Doppler processing unit 13, an image generating unit 14, an image memory 15, an internal storage unit 16, a volume-data processing unit 17, and a control unit 18.

The transmitting-receiving unit 11 includes a trigger generation circuit, a delay circuit, a pulser circuit, or the like, and provides a drive signal to the ultrasound probe 1. The pulser circuit repeatedly generates rate pulses for generating transmission ultrasound waves, at a predetermined rate frequency. The delay circuit gives, to each rate pulse generated by the pulser circuit, a delay time that is needed to converge the ultrasound waves generated by the ultrasound probe 1 into a beam and to determine the transmission directivity of each piezoelectric transducer. The trigger generation circuit applies the drive signal (drive pulse) to the ultrasound probe 1 at a timing based on the rate pulse. That is, the delay circuit changes the delay time to be given to each rate pulse to thereby arbitrarily adjust the transmission direction from the piezoelectric transducer surface.

The transmitting-receiving unit 11 has a function of instantly changing a transmission frequency, a transmission driving voltage, or the like in order to execute a predetermined scan sequence in accordance with an instruction from the control unit 18 to be described below. In particular, the transmission driving voltage is changed by a linear amplifier type transmission circuit that can instantly switch between values or by a mechanism that electrically switches between a plurality of power supply units.

The transmitting-receiving unit 11 includes an amplifier circuit, an A/D converter, an adder, or the like, and generates reflected wave data by performing various processes on the reflected wave signals received by the ultrasound probe 1. The amplifier circuit amplifies the reflected wave signals for each channel to thereby perform a gain correction process. The A/D converter performs A/D conversion on the reflected wave signals that have been subjected to the gain correction and gives a delay time, which is needed to determine the reception directivity, to the digital data. The adder performs an addition process on the reflected wave signals that have been processed by the A/D converter to thereby generate reflected wave data. By the addition process performed by the adder, reflection components from the direction according to the reception directivity of the reflected wave signals are intensified.

In this manner, the transmitting-receiving unit 11 controls the transmission directivity and the reception directivity in transmission and reception of ultrasound waves. The transmitting-receiving unit 11 according to the embodiment causes the ultrasound probe 1 to three-dimensionally transmit ultrasound beams to the subject P and generates three-dimensional reflected wave data from the three-dimensional reflected wave signals received by the ultrasound probe 1.

The B-mode processing unit 12 receives the reflected wave data from the transmitting-receiving unit 11 and performs logarithmic amplification, an envelope detection process, or the like, to thereby generate data (B-mode data) in which the signal strength is represented by luminance.

The Doppler processing unit 13 performs frequency analysis on velocity information on the basis of the reflected wave data received from the transmitting-receiving unit 11, extracts bloodstream, tissue, and contrast media echo components by the Doppler effect, and generates data (Doppler data) based on moving-object information, such as an average velocity, distribution, or power, extracted at multiple points.

The B-mode processing unit 12 and the Doppler processing unit 13 according to the embodiment can process both of the two-dimensional reflected wave data and the three-dimensional reflected wave data. Specifically, the B-mode processing unit 12 according to the embodiment can generate three-dimensional B-mode data from the three-dimensional reflected wave data. Furthermore, the Doppler processing unit 13 according to the embodiment can generate three-dimensional Doppler data from the three-dimensional reflected wave data.

The image generating unit 14 generates an ultrasound image from the data generated by the B-mode processing unit 12 and the Doppler processing unit 13. Specifically, the image generating unit 14 generates a B-mode image in which the intensities of the reflected waves are represented by luminance, from the B-mode data generated by the B-mode processing unit 12. More specifically, the image generating unit 14 generates a three-dimensional B-mode image from the three-dimensional B-mode data generated by the B-mode processing unit 12.

The image generating unit 14 also generates a color Doppler image as an average velocity image, a distribution image, a power image, or a combination image of the above images, each of which indicates moving body information in an imaging target portion, for example, information about a blood flow, from the Doppler image generated by the Doppler processing unit 13. Specifically, the image generating unit 14 generates a three-dimensional color Doppler image from the three-dimensional Doppler data generated by the Doppler processing unit 13.

In the following, the three-dimensional B-mode image generated by the image generating unit 14 is described as "volume data". That is, the image generating unit 14 has a function of generating the volume data.

The image generating unit 14 can also generate a composite image in which character information of various parameters, a scale, a body mark, and the like are synthesized to the ultrasound image.

Furthermore, the image generating unit 14 can generate various images for displaying the volume data on the monitor 2. Specifically, the image generating unit 14 can generate a Multi Planar Reconstructions (MPR) image or a rendering image (a volume rendering image or a surface rendering image) from ultrasound volume data.

The image memory 15 is a memory for storing the ultrasound image generated by the image generating unit 14. The image generating unit 14 stores, in the image memory 15, the volume data and a time taken for ultrasound scanning that is performed to generate the volume data, in association with an electrocardiogram transmitted from the electrocardiograph 4. That is, the volume-data processing unit 17, which will be described below, can acquire a cardiac phase at the time of the ultrasound scanning that is performed to generate the volume data, by referring to the data stored in the image memory 15. The image memory 15 can also store the data generated by the B-mode processing unit 12 and the Doppler processing unit 13.

The internal storage unit 16 stores therein control programs for performing ultrasound transmission/reception, image processing, and display processing; diagnosis information (for example, a patient ID or doctor's remarks); and various types of data, such as a diagnosis protocol and various body marks. The internal storage unit 16 is also used to store an image that is stored in the image memory 15, as needed basis. The data stored in the internal storage unit 16 can be transferred to an external peripheral device via an interface not illustrated.

The volume-data processing unit 17 is a processing unit that performs various types of image processing on the volume data stored in the image memory 15. As illustrated in FIG. 1, the volume-data processing unit 17 includes a motion information generating unit 17a and a calculating unit 17b. The processes performed by the volume-data processing unit 17 will be described in detail below.

The control unit 18 controls the entire process performed by the ultrasound diagnosis apparatus. Specifically, the control unit 18 controls processes performed by the transmitting-receiving unit 11, the B-mode processing unit 12, the Doppler processing unit 13, the image generating unit 14, and the volume-data processing unit 17, on the basis of various setting requests input from an operator via the input device 3 or various control programs and various types of data read from the internal storage unit 16. The control unit 18 controls display of an ultrasound image stored in the image memory 15, a GUI for specifying various processes performed by the volume-data processing unit 17, and a process result obtained by the volume-data processing unit 17, on the monitor 2.

The overall configuration of the ultrasound diagnosis apparatus according to the embodiment is explained above. With this configuration, the ultrasound diagnosis apparatus according to the embodiment generates volume data and performs image processing on the generated volume data. Specifically, the ultrasound diagnosis apparatus according to the embodiment generates volume data of the heart of the subject P. Then, the ultrasound diagnosis apparatus according to the embodiment performs image processing on the volume data of the heart of the subject P to thereby generate and display data that is used to determine the application of Cardiac Resynchronization Therapy (CRT) in advance or to evaluate the effect of the therapy.

Meanwhile, factors for determining whether to apply CRT or not or evaluating the effect of CRT include the degree of atrioventricular wall motion synchrony (between the left atrium and the left ventricle) or interventricular wall motion synchrony (between the right ventricle and the left ventricle), in addition to the degree of left ventricular wall motion synchrony.

Recent CRT devices have the flexibility to make settings for adjusting an atrioventricular delay (A-V delay) time and the flexibility to make settings for adjusting a ventricular delay (V-V delay) time, depending on the degree of dyssynchrony of the above factors. For example, a CRT device can set the atrioventricular delay time in the range "from 50 milliseconds to 160 milliseconds" at intervals of about 20 milliseconds and can set the ventricular delay time in the range "from −40 milliseconds to +40 milliseconds" at intervals of about 30 milliseconds.

When CRT is performed, it is needed to determine the initial setting (therapy plan) for CRT by optimizing the settings of the atrioventricular delay time and the ventricular delay time. Furthermore, to perform therapy evaluation by evaluating the degree of improvement in the dyssynchrony after the CRT therapy and give feedback in order to determine the optimal settings of the atrioventricular delay time and the ventricular delay time, it is needed to precisely evaluate differences in functions or wall motion timing between the ventricles or between the atrium and the ventricle. In this case, three-dimensional analysis using the volume data that can cover the whole myocardial region in the chambers can enable highly-precise evaluation without oversight, compared with two-dimensional analysis using a two-dimensional ultrasound image.

Therefore, the ultrasound diagnosis apparatus according to the embodiment generates volume data by three-dimensionally scanning the heart of the subject P with ultrasound waves.

When the external ultrasound probe 1 that performs sector scanning performs three-dimensional scanning of the whole heart of the subject P, because a cardiac apex cannot be visualized by a parasternal approach due to a limited acoustic window, an apical approach is employed. However, in the sector scanning using the apical approach, a visible width of the cardiac apex that is a shallow site becomes narrow.

Furthermore, the heart of a patient who has heart failure and to whom CRT is applied is often enlarged because of dilative compensation. In particular, Dilated Cardiomyopathy (DCM), in which the left ventricle is enlarged, often causes advanced heart failure, in which the Ejection Fraction (EF) significantly decreases, and also causes associated abnormality in the electrical conduction system as represented by left bundle branch block due to a wide range of myocardial damage; therefore, dyssynchrony is likely to occur. That is, with DCM, opportunities to diagnose the application of CRT increase.

Therefore, because the heart of the subject P for whom the application of CRT is diagnosed is often enlarged, it is difficult to simultaneously visualize myocardia in regions of both of the left and right sides of the heart in the cardiac apex region within an angle of view in the sector scanning using the apical approach.

Furthermore, in the three-dimensional scanning, needed reception scanning lines increase in proportion to the square of the multiplier compared to the two-dimensional scanning; therefore, temporal resolution (frame rate) becomes relatively insufficient because of the limitation of a sound velocity. Therefore, if the angle of view in the three-dimensional scanning is to be increased, it becomes difficult to ensure the temporal resolution. However, to evaluate the dyssynchrony that is a factor to determine the application of CRT, it is desirable to obtain the highest possible temporal resolution.

Furthermore, because the set duration of the delay time of the CRT device described above is, for example, about 20 milliseconds to 30 milliseconds, three-dimensional scanning is often set so that high temporal resolution in the three-dimensional scanning can be maintained. For example, an ideal setting of the three-dimensional scanning is 30 fps (frame per second), with reference to the reciprocal of the set duration. To obtain the high temporal resolution as described above, if the angle of view is narrowed in the settings, it is possible to relatively increase a scanning line density, so that it becomes possible to perform evaluation by using an image (volume data) with high spatial resolution.

However, it is practically difficult for the external ultrasound probe 1 to perform three-dimensional scanning with a wide angle of view that can simultaneously cover both of the right ventricle and the left ventricle when, for example, evaluating the application of CRT. Therefore, to evaluate interventricular dyssynchrony for the determination of the application of CRT through the three-dimensional scanning by the external ultrasound probe 1, it is needed to separately collect volume data including the left ventricle side and volume data including the right ventricle side by limiting the angle of view. Specifically, it is needed to divide the whole heart into two regions and separately collect the volume data in order to maintain needed temporal resolution and spatial resolution to evaluate the interventricular dyssynchrony for the determination of the application of CRT.

Figure 2:
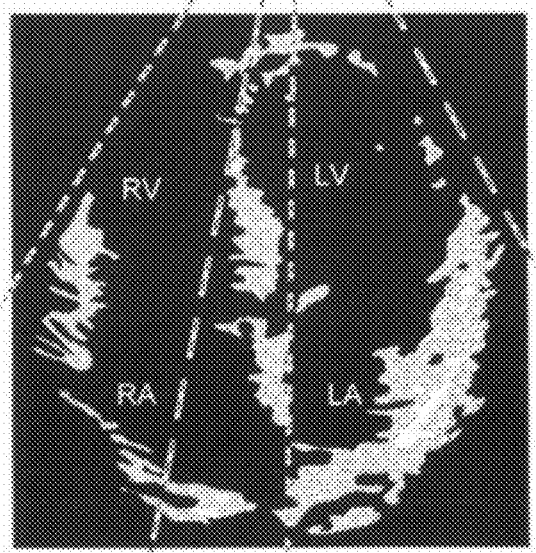
FIG. 2 is a diagram for explaining a first volume data group and a second volume data group.

Therefore, the ultrasound diagnosis apparatus according to the embodiment acquires a first volume data group that includes a region related to the left side of the heart and a second volume data group that includes a region related to the right side of the heart, from the volume data that is generated by three-dimensionally scanning the heart of the subject P with ultrasound waves for a duration of one or more heartbeats. Specifically, the ultrasound diagnosis apparatus according to the embodiment divides the heart of the subject P into a region including the left side of the heart and a region including the right side of the heart, and three-dimensionally scans each region with ultrasound waves for a duration of one or more heartbeats, thereby generating two volume data groups, i.e., the first volume data group and the second volume data group. FIG. 2 is a diagram for explaining the first volume data group and the second volume data group.

More specifically, the ultrasound probe 1 three-dimensionally scans the region including the left side of the heart with ultrasound waves for the duration of one or more heartbeats. Thereafter, the B-mode processing unit 12 generates a three-dimensional B-mode data of the region including the left side of the heart for the duration of one or more heartbeats. Then, the image generating unit 14 generates a plurality of pieces of volume data (the first volume data group) that are captured in a region 1 surrounded by dashed lines in FIG. 2, i.e., the Left Atrium (LA) and the Left Ventricular (LV), in a chronological order for the duration of one or more heartbeats.

Furthermore, the ultrasound probe 1 three-dimensionally scans the region including the right side of the heart with ultrasound waves for the duration of one or more heartbeats, at a different time from the time when the ultrasound scanning is performed to generate the first volume data group. Accordingly, the B-mode processing unit 12 generates three-dimensional B-mode data of the region including the right side of the heart for the duration of one or more heartbeats. Then, the image generating unit 14 generates a plurality of pieces of volume data (the second volume data group) that are captured in a region 2 surrounded by dotted lines in FIG. 2, i.e., the Right Atrium (RA) and the Right Ventricular (RV), in a chronological order for the duration of one or more heartbeats.

The image generating unit 14 then stores the first volume data group and the second volume data group in the image memory 15. Specifically, the image generating unit 14 stores the first volume data group, in which an ultrasound scanning duration is associated with each volume data, and an ECG at the time of generation of the first volume data group, in the image memory 15. Furthermore, the image generating unit 14 stores the second volume data group, in which an ultrasound scanning duration is associated with each volume data, and an ECG at the time of generation of the second volume data group, in the image memory 15. When receiving an image processing request from an operator via the input device 3, the control unit 18 causes the volume-data processing unit 17 to start processes.

Specifically, the motion information generating unit 17a included in the volume-data processing unit 17 generates first motion information that is information on cardiac wall motion in at least one of the left ventricle and the left atrium, from the first volume data group. The motion information generating unit 17a also generates second motion information that is information on cardiac wall motion in at least one of the right ventricle and the right atrium, from the second volume data group.

Figure 3:
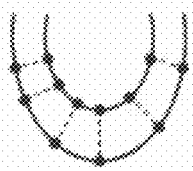
FIG. 3 is a diagram for explaining speckle tracking performed by a motion information generating unit.

More specifically, the motion information generating unit 17a tracks tracking points that are set on myocardial tissue visualized in each volume data, on the basis of a speckle pattern, thereby generating the first motion information and the second motion information. That is, the motion information generating unit 17a performs three-dimensional speckle tracking to generate the first motion information and the second motion information. FIG. 3 is a diagram for explaining the speckle tracking performed by the motion information generating unit.

For example, the input device 3 receives, from an operator, a request to display volume data of a first frame of the first volume data group and volume data of a first frame of the second volume data group. The control unit 18 that has received the transferred display request reads out, from the image memory 15, each volume data specified by the display request and displays the volume data on the monitor 2. For example, the control unit 18 causes the image generating unit 14 to generate a plurality of MPR images that are obtained by cutting each volume data specified by the display request at the cross sections in a plurality of directions, and displays the images on the monitor 2.

The operator sets a plurality of tracking points for performing tracking, on the endocardium and the epicardium as illustrated in FIG. 3, by referring to the volume data (for example, the MPR images generated by the image generating unit 14) displayed on the monitor. As illustrated in FIG. 3, the tracking points on the endocardium and the epicardium are set as pairs. The operator sets a plurality of tracking points on each of the MPR images to three-dimensionally track each of the left side of the heart and the right side of the heart. For example, the operator firstly traces the positions of the endocardium and the epicardium. Subsequently, the system reconstructs three-dimensional boundary surfaces from the traced surfaces of the endocardium and the epicardium, sets a mesh that is made up of a plurality of rectangles on each of the endocardium and the epicardium, and sets the vertexes of the rectangles as the tracking points.

Thereafter, the motion information generating unit 17a performs speckle tracking of the tracking points that are set in the volume data of the first frame of the first volume data group, for each volume data contained in the first volume data group, thereby generating the first motion information. Furthermore, the motion information generating unit 17a performs speckle tracking of the tracking points that are set in the volume data of the first frame of the second volume data, for each volume data contained in the second volume data group, thereby generating the second motion information. Specifically, the motion information generating unit 17a identifies correspondence between each of the tracking points that are set in the volume data of the first frame and a position in the volume data of other frames, through the speckle tracking.

Meanwhile, the motion information generating unit 17a, adds information on an ultrasound scanning duration and a cardiac phase by referring to the duration of the ultrasound scanning that is performed to generate each volume data and referring to the echocardiogram that is transmitted from the electrocardiograph 4, thereby generating the first motion information and the second motion information.

The first motion information may be information on the cardiac wall motion of the "left ventricle", information on the cardiac wall motion of the "left atrium", or information on the cardiac wall motion of both of the "left ventricle" and the "left atrium", depending on the locations of the tracking points that are set by the operator. Furthermore, the second motion information may be information on the cardiac wall motion of the "right ventricle", information on the cardiac wall motion of the "right atrium", or information on the cardiac wall motion of both of the "right ventricle" and the "right atrium", depending on the locations of the tracking points that are set by the operator.

Specifically, when analyzing the interventricular wall motion, the operator sets the tracking points so that the first motion information corresponds to the information on the wall motion of the "left ventricle" and the second motion information corresponds to the wall motion of the "right ventricle". Furthermore, when analyzing the interatrial wall motion, the operator sets the tracking points so that the first motion information corresponds to the information on the wall motion of the "left atrium" and the second motion information corresponds to the wall motion of the "right atrium". Moreover, when analyzing all of the interventricular wall motion, the interatrial wall motion, and the atrioventricular wall motion, the operator sets the tracking points so that the first motion information corresponds to the information on the wall motion of both of the "left ventricle" and the "left atrium" and the second motion information corresponds to the information on the wall motion of both of the "right ventricle" and the "right atrium".

The tracking points may be manually set by the operator as described above, or may be automatically set by the motion information generating unit 17a by extracting feature points in the volume data.

Concrete examples of the cardiac wall motion information generated by the motion information generating unit 17a will be explained below with reference to FIGS. 4A and 4B. FIGS. 4A and 4B are diagrams for explaining the concrete examples of the cardiac wall motion information generated by the motion information generating unit. Information shown in FIG. 4A is information on overall wall motion of a ventricle or an atrium, and information shown in FIG. 4B is information on regional wall motion of a ventricle or an atrium.

The motion information generating unit 17a generates information on the volume of at least one of a ventricle and an atrium, as the first motion information and the second motion information. Specifically, the motion information generating unit 17a identifies a three-dimensional region surrounded by the tracking points on the endocardium and a three-dimensional region surrounded by the tracking points on the epicardium, thereby generating the information related to the volume. More specifically, as illustrated in FIG. 4A, the motion information generating unit 17a calculates, as the first motion information and the second motion information, an end diastole volume "EDV (mL)" as an intracavity volume at the phase of an end diastole (ED) and an end systole volume "ESV (mL)" as an intracavity volume at the phase of an end systole (ES). Furthermore, as illustrated in FIG. 4A, the motion information generating unit 17a calculates, as the first motion information and the second motion information, an ejection fraction "EF (%)" that is defined by EDV and ESV.

Moreover, as illustrated in FIG. 4A, the motion information generating unit 17a calculates, as the first motion information and the second motion information, a "myocardial volume (mL)", a "myocardial mass (g)", and "Mass-Index $(g/m^2)$". Specifically, the motion information generating unit 17a calculates the "myocardial volume (mL)" by subtracting the volume inside the endocardium from the volume inside the epicardium. The myocardial volume changes with the heartbeats; however, the degree of a change in the myocardial volume over time is small. Therefore, for example, the motion information generating unit 17a calculates, as a representative myocardial volume, an average of the myocardial volumes calculated from respective pieces of volume data or a maximum value during one heartbeat.

The motion information generating unit 17a calculates the "myocardial mass (g)" by multiplying the "myocardial volume (mL)" by an average myocardial density value (for example, 1.05 g/mL). For example, the motion information generating unit 17a calculates the myocardial mass from an average myocardial volume. The motion information generating unit 17a calculates the "Mass-Index $(g/m^2)$" by normalizing the "myocardial mass (g)" by a "body surface area (BSA) $(m^2)$".

Meanwhile, the end diastole volume, the end systole volume, the ejection fraction, the myocardial volume, the myocardial mass, and the Mass-Index are representative values indicating information on the overall cardiac wall motion of a ventricle or an atrium at one heartbeat. By contrast, the intracavity volume changes over time in reflection of the pump function of an objective cardiac cavity, so that a temporal change curve of the intracavity volume becomes an important index for evaluating cardiac functions. Therefore, as illustrated in FIG. 4A, the motion information generating unit 17a generates a "temporal change curve of the intracavity volume". Specifically, the motion information generating unit 17a generates a graph on which the intracavity volume is plotted along a time axis, as the "temporal change curve of the intracavity volume". In other words, the "temporal change curve of the intracavity volume" is ""temporal change information" that is made up of a plurality of measured values along the time axis and that indicates a temporal change in the cardiac wall motion".

Furthermore, the motion information generating unit 17a generates, as the first motion information and the second motion information, regional strain (myocardial strain), a regional strain rate (myocardial strain rate), a regional displacement of myocardial tissue (myocardial displacement: displacement), or a velocity of the regional displacement of the myocardial tissue (myocardial velocity) of at least one of a ventricle and an atrium. Specifically, the motion information generating unit 17a generates information on regional cardiac wall motion in a ventricle or an atrium as illustrated by example in FIG. 4B, on the basis of a length and a direction of a line connecting the tracking points that are set as a pair. More specifically, as illustrated in FIG. 4B, the motion information generating unit 17a generates "regional myocardial strain (%)" and a "regional myocardial strain rate (1/s)" that indicates a temporal change in the regional myocardial strain. Furthermore, as illustrated in FIG. 4B, the motion information generating unit 17a generates a "regional myocardial displacement (cm)" and a "regional myocardial velocity (cm/s)" that indicates a temporal change in the regional myocardial displacement.

The information on the regional cardiac wall motion may be generated after component separation. For example, in the case of a left ventricle, the motion information generating unit 17a generates the information on the regional cardiac wall motion after separating the vectors connecting the tracking points set as pairs into components in a long axis (Longitudinal) direction, in a peripheral (Circumferential) direction, and in a wall thickness (Radial) direction. The information on the regional cardiac wall motion illustrated by example in FIG. 4 is "temporal change information that is made up of a plurality of measured values along the time axis and that indicates a temporal change in the cardiac wall motion". The motion information generating unit 17a may generate, as the information on the regional cardiac wall motion that is the "temporal change information that is made up of a plurality of measured values along the time axis and that indicates a temporal change in the cardiac wall motion", a regional area change ratio of at least one of a ventricle and an atrium or a change rate of the regional area change ratio (area change rate) of at least one of a ventricle and an atrium, in addition to the information illustrated by example in FIG. 4B. In this case, the motion information generating unit 17a calculates, for example, the area of a regional region of the endocardium (area of each rectangle) at a reference cardiac phase (reference phase). Specifically, the motion information generating unit 17a calculates the area of each rectangle surrounded by a plurality of tracking points set on a mesh of the endocardium in the volume data at the reference phase. The motion information generating unit 17a then performs tracking of the tracking points in a temporal series of volume data to thereby calculate the area of a rectangle at each cardiac phase, and thereafter normalizes the area of each rectangle at each cardiac phase by the area of a corresponding rectangle at the reference phase to thereby obtain the regional area change ratio. Accordingly, the motion information generating unit 17a obtains the regional area change ratio (unit: %) that indicates how each rectangle is deformed in the temporal series of volume data. Alternatively, the motion information generating unit 17a calculates, as the information on the regional cardiac wall motion, a temporal change rate of the regional area change ratio. Specifically, the motion information generating unit 17a calculates the temporal change rate of the area change ratio by estimating a temporal differential value of the regional area change ratio.

Meanwhile, the motion information generating unit 17a generates a plurality of distribution images, in which the information on the regional cardiac wall motion is mapped to a predetermined image, in a chronological order in order to output the information on the regional cardiac wall motion. Specifically, the motion information generating unit 17a converts a value of the cardiac wall motion information obtained in each regional region to a color on the basis of an LUT (Look Up Table) that is set in advance, and generates a plurality of distribution images in which the color is mapped to a predetermined image, in a chronological order. For example, there are known color-distribution mapping methods such as a method of mapping a value of the cardiac wall motion information that is obtained in each regional region to a Polar-map or a method of mapping the cardiac wall motion information to a surface rendering image of the surface of an inner membrane. The motion information generating unit 17a also generates a temporal change curve that is a graph on which the information on the regional cardiac wall motion is plotted along a time axis, in order to output the information on the regional cardiac wall motion.

When outputting the information on the regional cardiac wall motion, the motion information generating unit 17a may output the distribution image or the temporal change curve after averaging the values of the information on the regional cardiac wall motion for each of 16 to 17 segments recommended by the American Society of Echocardiography (ASE). Examples of the sections recommended by the American Society of Echocardiography include an anterior-septum (ant-sept.), an anterior wall (ant.), a lateral wall (lat.), a posterior wall (post.), an inferior wall (inf.) and a septum (sept.).

Furthermore, the motion information generating unit 17a generates, as the first motion information and the second motion information, an overall area change ratio, a change rate of the overall area change ratio, overall strain (myocardial strain), an overall strain rate (myocardial strain rate), an overall displacement of myocardial tissue (myocardial displacement), or a velocity of the overall displacement of the myocardial tissue (myocardial velocity) of at least one of a ventricle and an atrium. Specifically, the motion information generating unit 17a calculates the overall area change ratio by averaging the values of a plurality of regional area change ratios calculated in the same volume data. The motion information generating unit 17a calculates a temporal change rate of the overall area change ratio by averaging the values of temporal change rates of a plurality of regional area change ratios calculated in the same volume data. The motion information generating unit 17a calculates the overall myocardial strain by averaging the values of a plurality of pieces of regional myocardial strain calculated in the same volume data. The motion information generating unit 17a calculates the overall myocardial strain rate by averaging the values of a plurality of regional myocardial strain rates calculated in the same volume data. The motion information generating unit 17a calculates the overall regional myocardial displacement by averaging the values of a plurality of regional myocardial displacements calculated in the same volume data. The motion information generating unit 17a calculates the overall regional myocardial velocity by averaging the values of a plurality of regional myocardial velocities calculated in the same volume data. The information on the overall cardiac wall motion based on the information on the regional cardiac wall motion can be used as an index for evaluating the pump function of a cardiac cavity.

It is desirable that the motion information generating unit 17a generates the above-mentioned cardiac wall motion information (the first motion information and the second motion information) by using an average of the values of a plurality of heartbeats in order to reduce the influence of the fluctuation of the heartbeats.

The type and the output form of the cardiac wall motion information are specified by an operator. The motion information generating unit 17a generates the cardiac wall motion information of the type specified by the operator, from the first volume data group and the second volume data group. Specifically, the motion information generating unit 17a generates the same type of the first motion information and the second motion information. Furthermore, the motion information generating unit 17a generates and outputs the first motion information and the second motion information, which are the temporal change information, in the specified output form.

The temporal change curve of the intracavity volume, the information on the regional cardiac wall motion, and the information on the overall cardiac wall motion based on the information on the regional cardiac wall motion are temporal change information. Specifically, when the type of the cardiac wall motion information is "the temporal change curve of the intracavity volume", "the information on the regional cardiac wall motion", or "the information on the overall cardiac wall motion based on the information on the regional cardiac wall motion", the motion information generating unit 17a generates the first motion information and the second motion information as the temporal change information that is made up of a plurality of measured values along the time axis and that indicates a temporal change in the cardiac wall motion. However, as described above, the first volume data group and the second volume data group are collected in a different period of time. That is, the timing of collecting each volume data group is not the same. Furthermore, the setting of a needed angle of view may be different between imaging of the left side of the heart and imaging of the right side of the heart. Therefore, there may be fluctuation in the cardiac phase corresponding to each volume data (frame) between the volume data groups. Even if each volume data group is obtained at the completely same heart rate, when the setting of the angle of view is different between the imaging of the left side of the heart and the imaging of the right side of the heart, a frame-rate setting may vary, resulting in a difference in the cardiac phase corresponding to each frame between the volume data groups.

However, to accurately evaluate interventricular dyssynchrony or interatrial dyssynchrony, the cardiac phases in an analysis result related to both of the volume data groups, i.e., the cardiac phases in the first motion information and the second motion information that are the temporal change information, need to be associated with each other in a synchronous manner.

Therefore, when the first motion information and the second motion information generated by the motion information generating unit 17a are to be displayed on the monitor 2, and if the first motion information and the second motion information to be displayed are the temporal change information, the control unit 18 illustrated in FIG. 1 controls to display of first correction information and second correction information that are obtained by correcting the first motion information and the second motion information, which are displaying objects, such that they are substantially synchronized with each other in accordance with a cardiac phase. Specifically, the motion information generating unit 17a generates the first correction information and the second correction information by correcting the first motion information and the second motion information, which are the displaying objects, so as to be substantially synchronized with each other on the basis of a cardiac phase, under the control by the control unit 18.

More specifically, the motion information generating unit 17a generates the first correction information and the second correction information by a first interpolation method or a second interpolation method explained below, under the control by the control unit 18.

The first interpolation method will be explained below. FIG. 5 is a diagram for explaining the first interpolation method performed by the motion information generating unit. In one example illustrated in FIG. 5, the first motion information and the second motion information, which are the temporal change information, are represented as data 1 and data 2, respectively (see the upper diagram in FIG. 5). Furthermore, in one example illustrated in FIG. 5, a frame interval of the first volume data group is denoted by "dT1" and a frame interval of the second volume data group is denoted by "dT2 (dT2<dT1)" (see the upper diagram in FIG. 5).

When performing the first interpolation method, the motion information generating unit 17a sets, as an origin, a measured value corresponding to a reference cardiac phase that is set in advance, from among the measured values contained in each motion information, thereby aligning start points of the first motion information and the second motion information that are the temporal change information.

For example, when an R-wave phase is set as the reference cardiac phase, the motion information generating unit 17a aligns the start points of the data 1 and the data 2 in accordance with the R-wave phase as illustrated in the lower diagram in FIG. 5. It is possible to set a P-wave phase, which is an origin of the atrial contraction, as the reference cardiac phase.

The motion information generating unit 17a then interpolates a measured value of one motion information at an elapsed time from the start point of the measured values contained in the other motion information, by using a measured value that is measured near the elapsed time in the one motion information. Consequently, the motion information generating unit 17a generates the first correction information and the second correction information.

For example, the motion information generating unit 17a sets the data 1 having a long frame interval as an interpolation object. The motion information generating unit 17a interpolates a measured value of the data 1 at an elapsed time from the R-wave phase (start point) of the measured values contained in the data 2, by using a measured value that is measured near the elapsed time in the data 1 (see a dashed-line circle shown in the lower diagram in FIG. 5). Consequently, the motion information generating unit 17a generates correction data of the data 1, in which the data interval is changed to the temporal resolution of "dT2" similarly to the data 2 (see black circles shown in the lower diagram in FIG. 5).

On the other hand, when performing the second interpolation method, the motion information generating unit 17a relatively adjusts durations between the reference cardiac phases, between the first motion information and the second motion information that are the temporal change information. Specifically, in the second interpolation method, the cardiac phases are matched with each other by using the systole. For example, in the second interpolation method, as illustrated in FIG. 6, because an Aortic Valve Close (AVC) phase is at a boundary between the ventricular systole and the ventricular diastole, the AVC time is defined as 100% separately for each of the first motion information and the second motion information. In the second interpolation method, it is possible to define the duration between the R-wave phases or between the P-wave phases, that is, one cardiac cycle, as 100%.

Then, the motion information generating unit 17a interpolates measured values at a plurality of relative elapsed times that are obtained by dividing the relatively-adjusted duration between the reference cardiac phases by a predetermined interval, by using a measured value that is measured near each of the relative elapsed times in each of the first motion information and the second motion information. Consequently, the motion information generating unit 17a generates the first correction information and the second correction information. More specifically, the motion information generating unit 17a divides the duration between the reference cardiac phases, which is relatively adjusted as 100%, by a value in a range "from 1% to 5%". For example, as illustrated in FIG. 6, the motion information generating unit 17a divides the AVC time of 100% into relative elapsed times by 5%.

Thereafter, as illustrated in FIG. 6, the motion information generating unit 17a obtains measured values at respective relative elapsed times at intervals of 5% in the first motion information for the duration of about 200% (or about 300%), though the interpolation using a plurality of measured values that are measured near the relative elapsed times. Similarly, the motion information generating unit 17a obtains measured values at respective relative elapsed times at intervals of 5% in the second motion information, though the interpolation using a plurality of measured values that are measured near the relative elapsed times.

To convert the relative elapsed time (%) to the absolute time (milliseconds), the motion information generating unit 17a multiples the relative elapsed time (%) by "AVC time/100" that is obtained when the first volume data is captured or "AVC time/100" that is obtained when the second volume data is captured.

In this manner, the motion information generating unit 17a generates the first correction information and the second correction information by correcting the first motion information and the second motion information, which are the temporal change information, such that they are substantially synchronized with each other in accordance with the cardiac phase, through the first interpolation method or the second interpolation method.

The control unit 18 controls so that the first correction information and the second correction information generated by the motion information generating unit 17a are displayed on the monitor 2. Specifically, the motion information generating unit 17a generates a motion information image, in which the first correction information and the second correction information are arranged along the time axis such that time phases are aligned on the basis of a predetermined cardiac phase. More specifically, the motion information image is a graph or a distribution image as explained below. The control unit 18 controls so that the motion information image is displayed on the monitor 2.

The first correction information and the second correction information to be displayed under the control by the control unit 18 will be explained below.

First, a case will be explained that the temporal change curve is displayed. The motion information generating unit 17a generates two graphs by separately plotting the first correction information and the second correction information along the time axis, under the control by the control unit 18. Specifically, the motion information generating unit 17a generates a plurality of temporal change curves as the first correction information and the second correction information and generates the motion information image by arranging the graphs such that the time phases of the temporal change curves are aligned. Then, the control unit 18 controls display of the two graphs generated by the motion information generating unit 17a side by side. When the first correction information and the second correction information that are the information on the regional cardiac wall motion are to be displayed as the temporal change curves, because each of the first correction information and the second correction information is made up of a plurality of pieces of information on the cardiac wall motion in a regional region, it is desirable to display separate graphs side by side.

Alternatively, the motion information generating unit 17a generates one graph by collectively plotting the first correction information and the second correction information along the time axis, under the control by the control unit 18. Specifically, the motion information generating unit 17a generates a plurality of temporal change curves as the first correction information and the second correction information and superimposes the temporal change curves in one graph, thereby generating a plurality of temporal change curves as the first correction information and the second correction information that form the motion information image. Then, the control unit 18 controls display of the one graph generated by the motion information generating unit 17a. For example, when "the temporal change curve of the intracavity volume" or "the information on the overall cardiac wall motion based on the information on the regional cardiac wall motion" is to be displayed as the temporal change curve, because the first correction information and the second correction information facilitate determination of the interventricular synchrony or the interatrial synchrony, it is desirable to display the information collectively in one graph.

Figure 7:
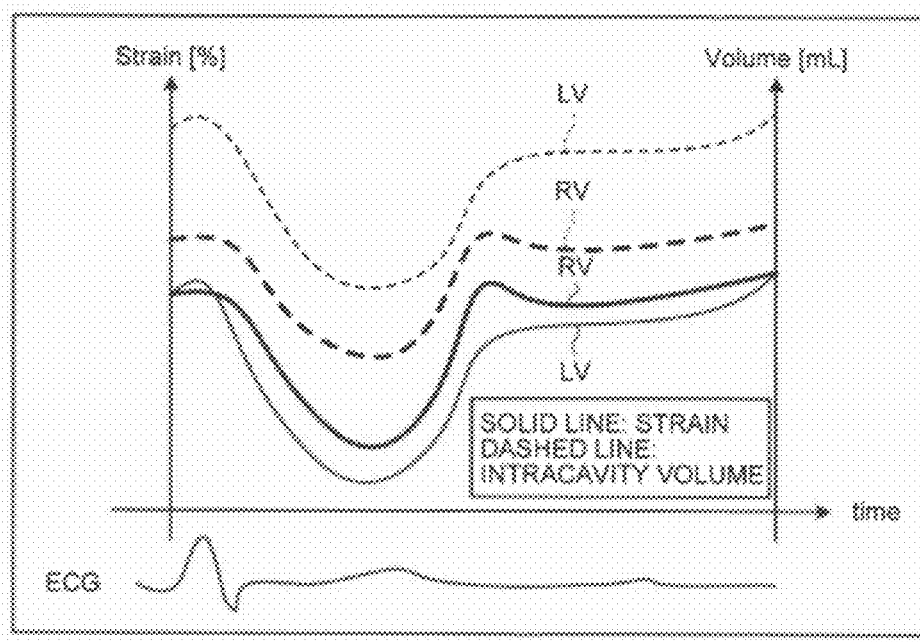
FIG. 7 is a diagram for explaining an example of a temporal change curve that is displayed in the embodiment.

Furthermore, when a plurality of temporal change curves of the intracavity volume or a plurality of pieces of the information on the overall cardiac wall motion based on the information on the regional cardiac wall motion are selected as displaying objects, a plurality of pairs of the first correction information and the second correction information are generated. In this case, it may be possible to generate and display one graph for each pair of the correction information or generate and display a graph in which the temporal change curves for the respective pairs of the correction information are gathered. FIG. 7 is a diagram for explaining one example of the temporal change curves that are displayed in the embodiment.

For example, the motion information generating unit 17a generates a motion information image as one graph, in which temporal change curves of the intracavity volumes of the left ventricle and the right ventricle (see dashed lines in FIG. 7) and temporal change curves of the overall myocardial strain in the longitudinal direction in the left ventricle and the right ventricle (see solid lines in FIG. 7) are gathered. As illustrated in FIG. 7, the motion information generating unit 17a may generate an image, in which ECG adjusted to the time axis of the graph is combined with the graph, as a motion information image. The control unit 18 controls display of the motion information image illustrated in FIG. 7 on the monitor 2.

The control unit 18 may display a value that is to be an index for determining the interventricular synchrony or the interatrial synchrony. Specifically, the calculating unit 17b illustrated in FIG. 1 calculates a difference between an extremum contained in the first correction information and an extremum contained in the second correction information. More specifically, the calculating unit 17b calculates a temporal difference between a time point corresponding to an extremum of the measured values contained in the first correction information and a time point corresponding to an extremum of the measured values contained in the second correction information. Then, the control unit 18 controls so that the temporal difference calculated by the calculating unit 17b is displayed on the monitor 2, in addition to the motion information image.

Figure 8:
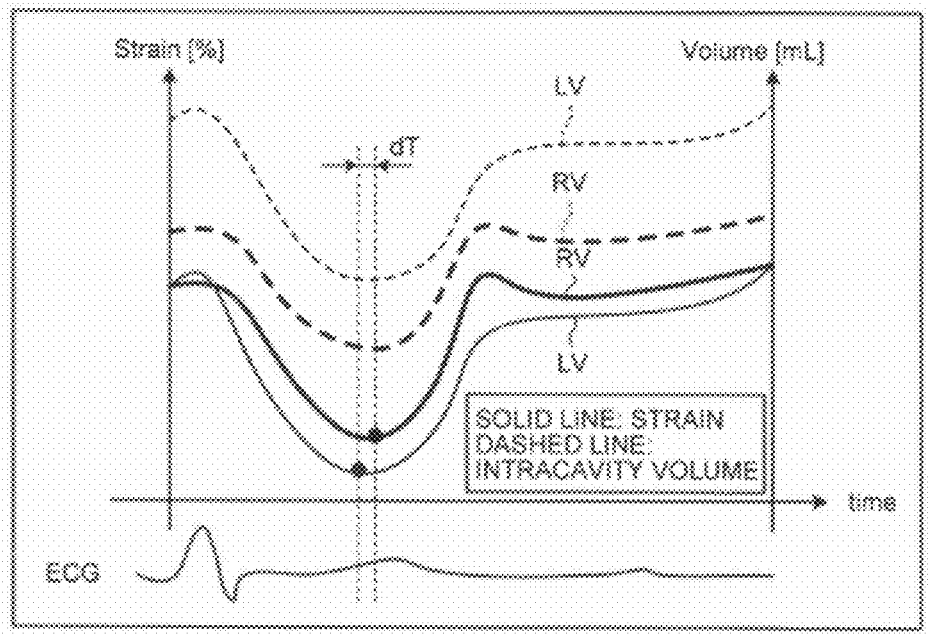
FIG. 8 is a diagram for explaining a calculating unit.

For example, as illustrated in FIG. 8, the calculating unit 17b calculates a temporal difference "dT" between a time point corresponding to the minimum value on the temporal change curve of the intracavity volume of the left ventricle and a time point corresponding to the minimum value on the temporal change curve of the intracavity volume of the right ventricle. Then, the control unit 1B controls display of the temporal difference "dT" on the graph in a superimposed manner.

A case will be explained that a distribution image is displayed as the motion information image. As described above, the distribution image is used to output the information on the regional cardiac wall motion. The motion information generating unit 17a generates a first distribution image group, in which the information on the regional cardiac wall motion in the first correction information is mapped along the time axis, under the control by the control unit 18. Furthermore, the motion information generating unit 17a generates a second distribution image group, in which the information on the regional cardiac wall motion in the second correction information is mapped along the time axis, under the control by the control unit 18.

Figure 9:
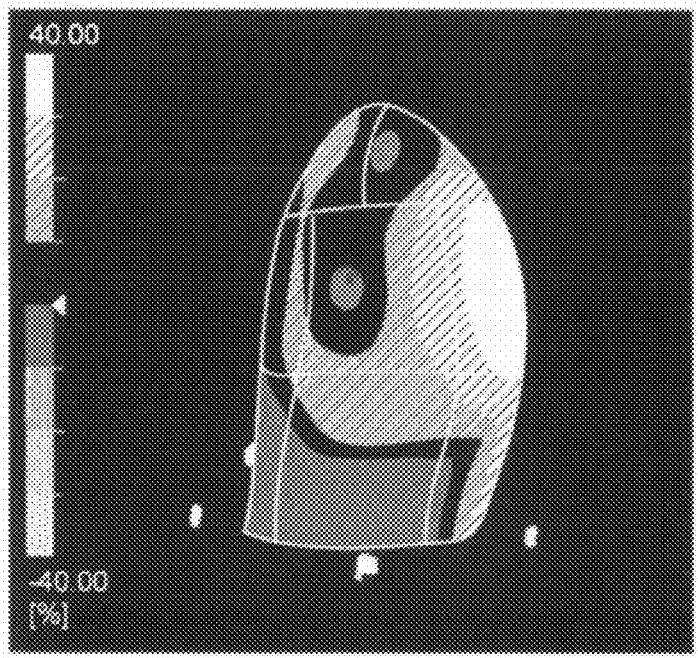
FIG. 9 is a diagram (1) for explaining an example of a distribution image that is displayed in the embodiment.
Figure 10:
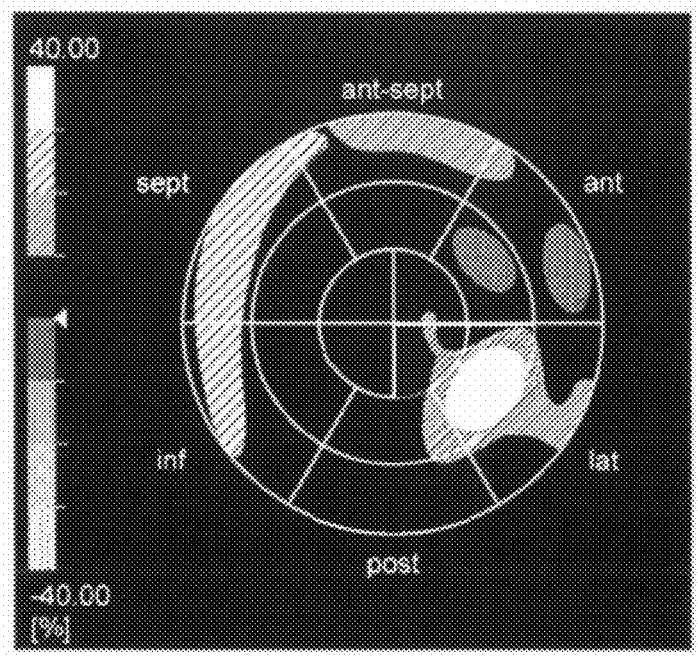
FIG. 10 is a diagram (2) for explaining an example of the distribution image that is displayed in the embodiment.

Thereafter, the control unit 18 controls display of moving images of the first distribution image group and the second distribution image group such that they are substantially synchronized with the cardiac phase. FIG. 9 and FIG. 10 are diagrams for explaining examples of the distribution images that are displayed in the embodiment.

For example, as illustrated in FIG. 9, the motion information generating unit 17a converts a value of the cardiac wall motion information obtained in each regional region in the first correction information to a color and thereafter generates the first distribution image group by mapping the color to a surface rendering image of the surface of the inner membrane. Similarly, the motion information generating unit 17a generates the second distribution image group by mapping the second correction information to a surface rendering image of the surface of the inner membrane. Alternatively, as illustrated in FIG. 10 for example, the motion information generating unit 17a converts a value of the cardiac wall motion information obtained in each regional region in the first correction information to a color and thereafter generates the first distribution image group by mapping the color to a Polar-map. Similarly, the motion information generating unit 17a generates the second distribution image group by mapping the second correction information to a Polar-map.

Figure 11:
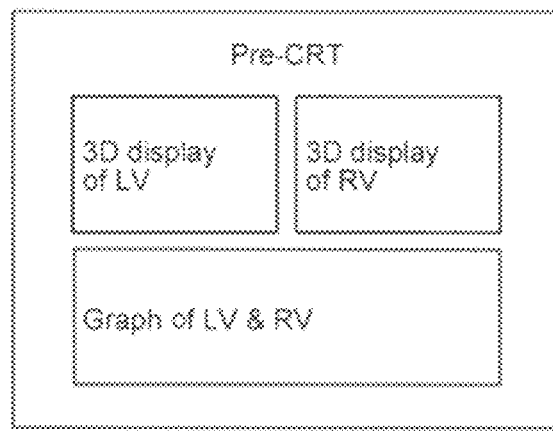
FIG. 11 is a diagram for explaining an example of an information layout that is displayed in the embodiment.

FIG. 11 is a diagram for explaining an example of an information layout that is displayed in the embodiment. For example, at the time of determination before CRT (Pre-CRT), the first distribution image group, in which the information on the regional cardiac wall motion of the left ventricle is mapped to the surface rendering image, is displayed as a three-dimensional moving image in an upper left region on the monitor 2 (see "3D display of LV" in the figure), under the control by the control unit 18. Furthermore, the second distribution image group, in which the information on the regional cardiac wall motion of the right ventricle is mapped to the surface rendering image, is displayed as a three-dimensional moving image in an upper right region on the monitor 2 (see "3D display of RV" in the figure), under the control by the control unit 18. Moreover, the temporal change curves (graph) illustrated in FIG. 7 or FIG. 8 are displayed in a lower half region on the monitor 2 (see "Graph of LV & RV) in the figure). The motion information generating unit 17a separately generates the first distribution image group, the second distribution image group, and the graph, and thereafter layouts them in three regions as illustrated by example in FIG. 11, thereby generating the motion information image.

Figure 12:
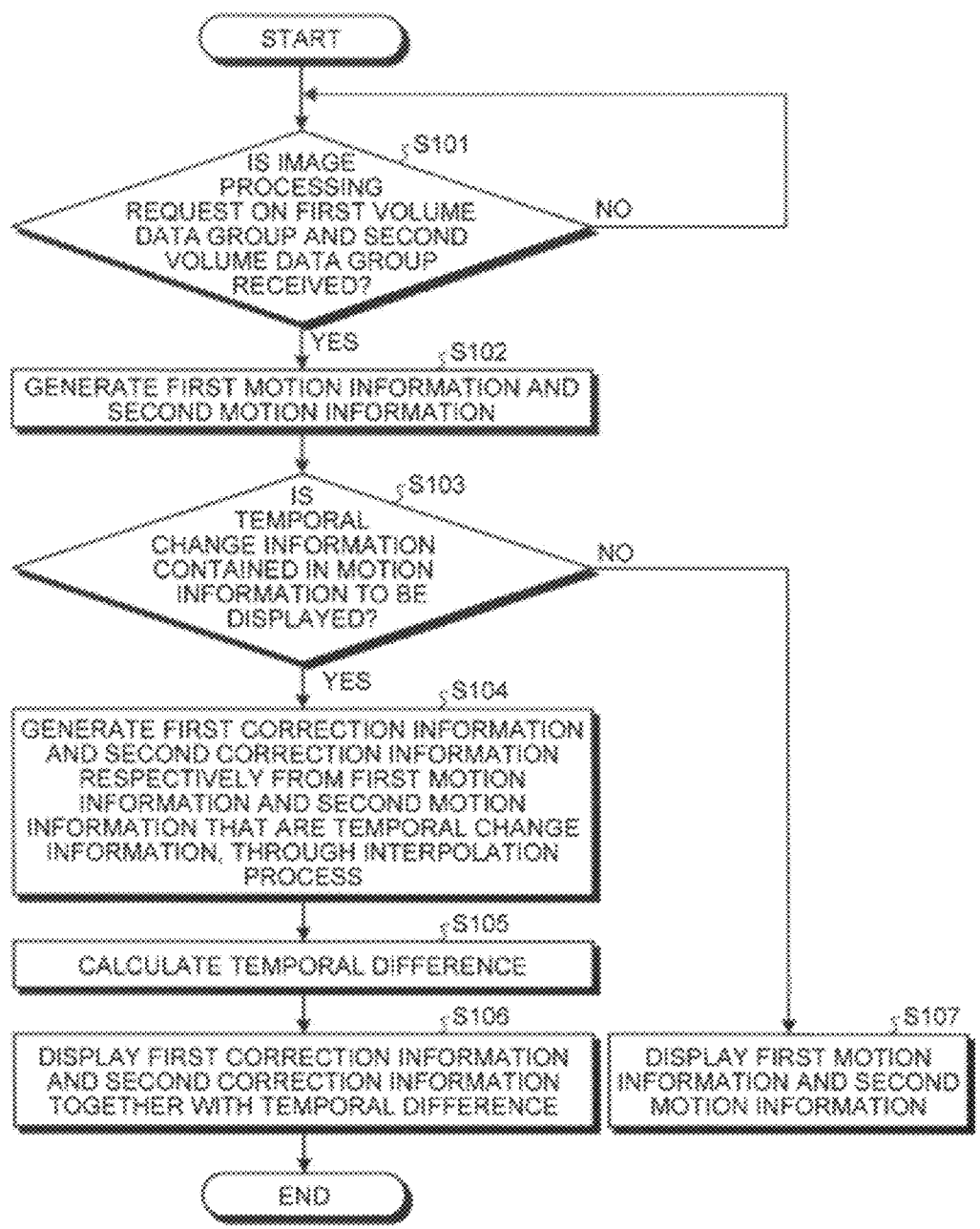
FIG. 12 is a flowchart for explaining a process performed by the ultrasound diagnosis apparatus according to the embodiment.

A process performed by the ultrasound diagnosis apparatus according to the embodiment will be explained below with reference to FIG. 12. FIG. 12 is a flowchart for explaining the process performed by the ultrasound diagnosis apparatus according to the embodiment. In the following, a process performed after the first volume data group and the second volume data group are stored in the image memory 15 will be explained.

As illustrated in FIG. 12, the ultrasound diagnosis apparatus according to the embodiment determines whether an image processing request on the first volume data group and the second volume data group is received from an operator via the input device 3 (Step S101). When the image processing request is not received (NO at Step S101), the ultrasound diagnosis apparatus enters a standby state.

On the other hand, when the image processing request is received (YES at Step S101), the motion information generating unit 17a performs a tracking process by using tracking points that are set by the operator, thereby generating the first motion information and the second motion information from the first volume data group and the second volume data group, respectively (Step S102).

The control unit 18 determines whether or not the motion information to be displayed contains temporal change information (Step S103). When the temporal change information is not contained (NO at Step S103), the control unit 18 controls display of the first motion information and the second motion information on the monitor 2 (Step S107) and terminates the process.

On the other hand, when the temporal change information is contained (YES at Step S103), the motion information generating unit 17a generates the first correction information and the second correction information respectively from the first motion information and the second motion information that are the temporal change information, through the interpolation process, i.e., through one of the first interpolation method and the second interpolation method (Step S104).

The calculating unit 17b calculates a temporal difference from the same type of the first correction information and the second correction information (Step S105). The control unit 18 controls display of the first correction information and the second correction information on the monitor 2 together with the temporal difference (Step S106) and terminates the process. At Step S106, when information other than the temporal change information is contained in the motion information to be displayed, the control unit 18 also controls display of this information.

As described above, according to the embodiment, the motion information generating unit 17a generates the first motion information, which is the information on the cardiac wall motion in at least one of the left ventricle and the left atrium, and the second motion information, which is the information on the cardiac wall motion in at least one of the right ventricle and the right atrium, respectively from the first volume data group and the second volume data group which are two volume data groups generated by three-dimensionally scanning a divided region of the heart of the subject P including the left side of the heart and a divided region of the heart of the subject P including the right side of the heart.

When the control unit 18 displays the first motion information and the second motion information generated by the motion information generating unit 17a on a predetermined display unit, and if the first motion information and the second motion information to be displayed are the temporal change information that indicates a temporal change in the cardiac wall motion and that is made up of a plurality of measured values along the time axis, the control unit 18 controls display of the first correction information and the second correction information that are obtained by correcting the first motion information and the second motion information, which are displaying objects, such that they are substantially synchronized with each other in accordance with a cardiac phase.

Specifically, according to the embodiment, it is possible to collect the first volume data group and the second volume data group at the spatial resolution and the temporal resolution that are optimal to each of the left side of the heart and the right side of the heart. Furthermore, according to the embodiment, it is possible to generate the first motion information and the second motion information respectively from the first volume data group and the second volume data group, each of which has the optimal spatial resolution and the optimal temporal resolution. Moreover, according to the embodiment, it is possible to simultaneously display the first motion information and the second motion information, which are the temporal change information, in such a manner that they are synchronized with the cardiac phase. That is, according to the embodiment, it is possible to three-dimensionally analyze the degree of interventricular or interatrial synchrony of the cardiac functions or the cardiac wall motion, in addition to the degree of left ventricular synchrony.

Therefore, according to the embodiment, it becomes possible to precisely and three-dimensionally analyze a difference in the interventricular wall motion synchrony, the interatrial wall motion synchrony, and the atrioventricular wall motion synchrony. In particular, in the dyssynchrony diagnosis for the application of CRT, a doctor can accurately evaluate a time lag (the degree of dyssynchrony) of the wall motion phase between the ventricles. Furthermore, according to the embodiment, a doctor can accurately set the atrioventricular delay time or the ventricular delay time of a CRT device. For example, a doctor can accurately make initial settings of the atrioventricular delay time or the ventricular delay time of the CRT device at the beginning of therapy or can accurately re-set the atrioventricular delay time and the ventricular delay time of the CRT device after evaluating the effect of the therapy.

Furthermore, according to the embodiment, the calculating unit 17b calculates a temporal difference between a time point corresponding to the extremum of the measured values contained in the first correction information and a time point corresponding to the extremum of the measured values contained in the second correction information, and the control unit 18 controls display of the temporal difference on the monitor 2. Therefore, according to the embodiment, a doctor can easily set the atrioventricular delay time and the ventricular delay time of the CRT device.

Moreover, according to the embodiment, the motion information generating unit 17a performs the first interpolation method. Specifically, the motion information generating unit 17a sets, as an origin, a measured value corresponding to the reference cardiac phase that is set in advance, from among the measured values contained in each motion information, thereby aligning the start points of the first motion information and the second motion information that are the temporal change information. Thereafter, the motion information generating unit 17a interpolates a measured value of one motion information at an elapsed time from the start point of the measured values contained in the other motion information, by using a measured value that is measured near the elapsed time in the one motion information, thereby generating the first correction information and the second correction information. That is, according to the embodiment, it becomes possible to generate the first correction information and the second correction information that are substantially synchronized with the cardiac phase, in accordance with, for example, the motion information with high temporal resolution.

Alternatively, according to the embodiment, the motion information generating unit 17a performs the second interpolation method. Specifically, the motion information generating unit 17a relatively adjusts the durations between the reference cardiac phases, between the first motion information and the second motion information that are the temporal change information; and thereafter interpolates measured values at a plurality of relative elapsed times that are obtained by dividing the relatively-adjusted duration between the reference cardiac phases by a predetermined interval, by using a measured value that is measured near each of the relative elapsed times in each of the first motion information and the second motion information. Specifically, according to the embodiment, the first motion information and the second motion information are normalized in accordance with "a clock of the heart", and thereafter the first correction information and the second correction information which have the same temporal resolution and in which the cardiac phases are substantially synchronized with each other are generated.

Furthermore, according to the embodiment, the motion information generating unit 17a generates the first motion information and the second motion information by tracking the tracking points set on the myocardial tissue visualized in each volume data, on the basis of a speckle pattern. Therefore, according to the embodiment, it is possible to easily generate the first motion information and the second motion information by using well-known techniques.

Moreover, according to the embodiment, the motion information generating unit 17a generates two graphs by separately plotting the first correction information and the second correction information along the time axis, and the control unit 18 controls to display of the two graphs side by side. Alternatively, the motion information generating unit 17a generates one graph by collectively plotting the first correction information and the second correction information along the time axis, and the control unit 18 controls to display of one graph.

Specifically, according to the embodiment, when, for example, the first correction information and the second correction information that are the information on the regional cardiac wall motion are to be displayed as the temporal change curves, it is possible to display them in separate graphs that are arranged side by side. Furthermore, according to the embodiment, when, for example, the temporal change curves of the intracavity volumes or the information on the overall cardiac wall motion based on the information on the regional cardiac wall motion is to be displayed as the temporal change curve, it is possible to collectively display them in one graph. Therefore, according to the embodiment, a doctor can select an optimal display form depending on the characteristics of the temporal change information to be displayed.

Moreover, according to the embodiment, the motion information generating unit 17a generates, as the first motion information and the second motion information, the information related to the volume of at least one of a ventricle and an atrium. The motion information generating unit 17a generates, as the first motion information and the second motion information, the overall strain, the overall strain rate, the overall displacement of myocardial tissue, or the overall displacement velocity of myocardial tissue of at least one of the ventricle and the atrium. Moreover, the motion information generating unit 17a generates, as the first motion information and the second motion information, the regional strain, the regional strain rate, the regional displacement of myocardial tissue, or the regional displacement velocity of myocardial tissue of at least one of the ventricle and the atrium. Therefore, according to the embodiment, it is possible to exhaustively provide a doctor with various indices of three-dimensional analysis of the cardiac wall motion.

The ultrasound diagnosis apparatus according to the embodiment may be implemented as the following two modifications.

A first modification will be explained below. For example, if the above processes are performed on a first volume data group and a second volume data group that are captured after CRT (Post-CRT), it becomes possible to easily evaluate the effect of CRT. However, when evaluating the effect of CRT, it is desirable to simultaneously refer to information on processes performed on a first volume data group and a second volume data group that are captured before CRT (Pre-CRT).

Figure 13:
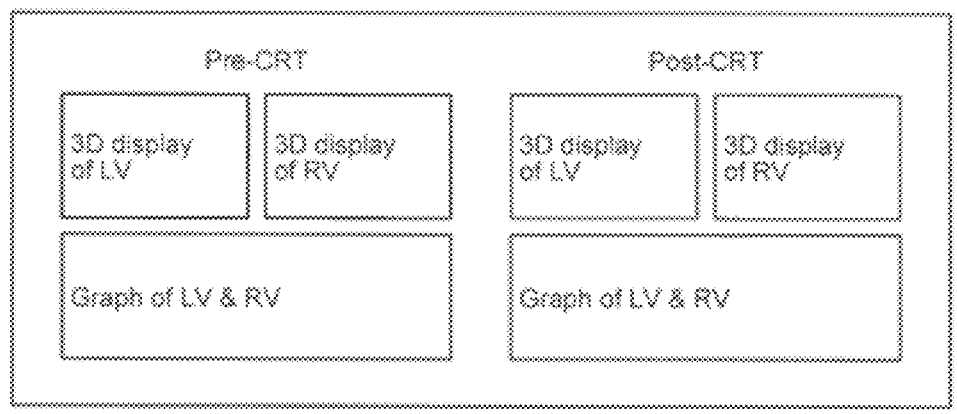
FIG. 13 is a diagram (1) for explaining a first modification of the embodiment.
Figure 14:
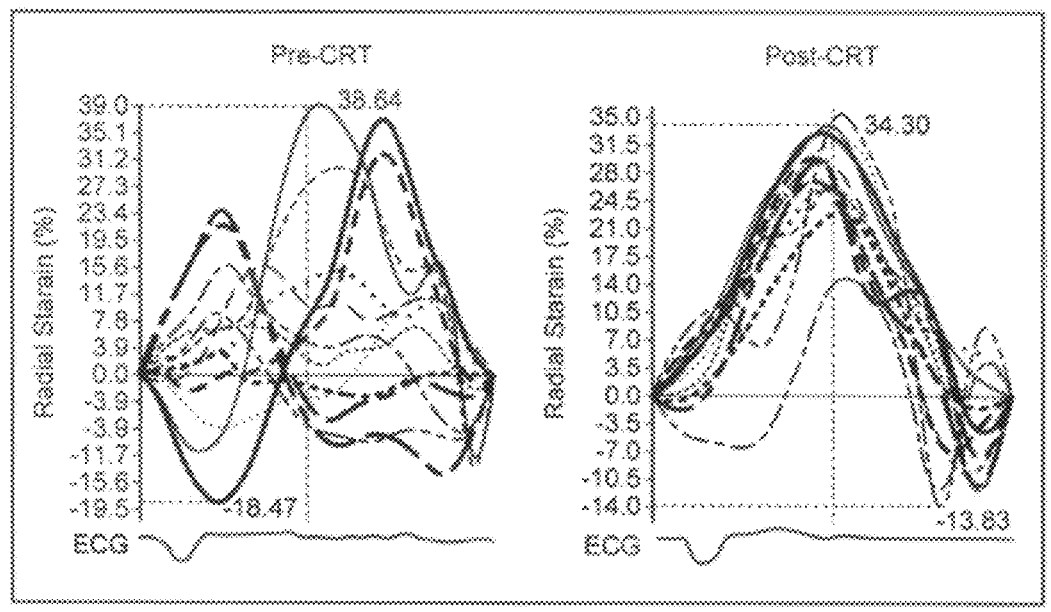
FIG. 14 is a diagram (2) for explaining the first modification of the embodiment.

Therefore, in the first modification, in which a plurality of pairs of volume data, each of which is a pair of the first volume data group and the second volume data group, are formed by performing three-dimensional scanning at a plurality of different times, the motion information generating unit 17a performs the following process. Specifically, the motion information generating unit 17a generates correction information pairs, each of which is formed of the first correction information and the second correction information, for the respective pairs of the volume data, and generates motion information image pairs from the correction information pairs. Thereafter, the control unit 18 controls to display of the motion information image pairs generated by the motion information generating unit 17a on the monitor 2 side by side. FIG. 13 and FIG. 14 are diagrams for explaining the first modification of the embodiment.

For example, each of the motion information image based on the correction information before CRT (Pre-CRT) and the motion information image based on the correction information after CRT (Post-CRT) is arranged in the layout as illustrated by example in FIG. 11. However, the first distribution image group, the second distribution image group, and the temporal change curve that are the correction information before CRT (Pre-CRT) are displayed in the left half region of the monitor 2 as illustrated in FIG. 13. Furthermore, the first distribution image group, the second distribution image group, and the temporal change curve that are the correction information after CRT (Post-CRT) are displayed on the right half region of the monitor 2 as illustrated in FIG. 13.

Alternatively, as illustrated in FIG. 14, the control unit 18 controls to display of a graph, in which a regional strain in the radial direction (radial-strain) in the left ventricle before CRT is plotted, and a graph, in which a regional strain in the radial direction (radial-strain) in the left ventricle after CRT is plotted, side by side.

Therefore, according to the first modification, a doctor can easily recognize the degree of improvement in the interventricular dyssynchrony or the interatrial dyssynchrony before and after the therapy. Consequently, it is possible to effectively evaluate the effect of the therapy.

A second modification will be explained below. As described above, the first volume data group and the second volume data group are groups of data collected from the left side of the heart and the right side of the heart with the optimal spatial resolution and the optimal temporal resolution. Therefore, in the second modification, the motion information generating unit 17a generates the first motion information or the second motion information by taking one of the first volume data group and the second volume data group as a processing object. The control unit 18 controls to display of the first motion information or the second motion information generated by the motion information generating unit 17a on the monitor 2. Even in the second modification, the calculating unit 17b may calculate a temporal difference between the extremum on the temporal change curve of the left ventricle and the extremum on the temporal change curve of the left atrium or a temporal difference between the extremum on the temporal change curve of the right ventricle and the extremum on the temporal change curve of the right atrium. Furthermore, even in the second modification, it is possible to display pieces of motion information obtained before and after CRT, side by side.

That is, in the second modification, it is possible to compare and determine the synchrony between the left ventricle and the left atrium or the synchrony between the right ventricle and the right atrium without performing the interpolation process.

Consequently, in the second modification, it becomes particularly possible to three-dimensionally analyze a difference in atrioventricular cardiac functions or a difference in the timing of atrioventricular wall motion. In particular, a doctor can accurately evaluate a time lag (the degree of dyssynchrony) of the wall motion phase between the atrium and ventricle when diagnosing the dyssynchrony for the application of CRT.

In the above embodiments, a case has been explained that the ultrasound diagnosis apparatus performs the processes on the volume data groups. However, there may be a case that an image processing apparatus that is installed independent of the ultrasound diagnosis apparatus performs the processes on the above-mentioned volume data groups. Specifically, there may be a case that an image processing apparatus provided with the volume-data processing unit 17 and a display control function of the control unit 18 illustrated in FIG. 1 receives two volume data groups that have been received from the ultrasound diagnosis apparatus, a PACS database, or a database of an electronic health chart system and thereafter performs the above-mentioned image processing.

Each of the components of the apparatuses depicted in the drawings is based on a functional concept and does not necessarily need to be physically configured as depicted in the drawings. Specific forms of disintegration and integration of each of the apparatuses and devices are not limited to the one depicted in the drawings. It is possible that all or some of the apparatuses and devices be functionally or physically disintegrated or integrated into any part depending on load or usage. For example, the correction information generation process and the motion information image generation process performed by the motion information generating unit 17a may be performed by a processing unit that is different form the motion information generating unit 17a. The image processing method explained in the embodiments may be implemented by causing a computer, such as a personal computer or a workstation, to execute an image processing program that is prepared in advance. The image processing program can be distributed via a network, such as the Internet. The image processing program may be stored in a computer-readable recording medium, such as a hard disk, a flexible disk (FD), a CD-ROM, an MO, or a DVD, so that the computer can read out and execute the programs from these media.

As described above, according to the embodiments, it is possible to three-dimensionally and precisely analyze a difference in the interventricular wall motion synchrony, the interatrial wall motion synchrony, and the atrioventricular wall motion synchrony.

While certain embodiments have been described, these embodiments have been presented by way of examples only, and are not intended to limit the scope of the invention. Indeed, the novel embodiments described herein may be embodied in a variety of other forms; furthermore, various omissions, substitutions, and changes in the form of the apparatus and method described herein may be made without departing from the spirit of the invention. The accompanying claims and their equivalents are intended to cover such forms or modifications as would fall within the scope and spirits of the invention.

What is claimed is:

1. An ultrasound diagnosis apparatus comprising:
an image generating unit configured to obtain a first volume data group including a region related to a left side of a heart of a subject and a second volume data group including a region related to a right side of the heart from volume data that is generated by three-dimensionally scanning the heart of the subject with an ultrasound wave for a duration of one or more heartbeats;
a motion information generating unit configured to
generate first motion information on cardiac wall motion of at least one of a left ventricle and a left atrium and second motion information on cardiac wall motion of at least one of a right ventricle and a right atrium, each of the first motion information and the second motion information being temporal change information that is made up of a plurality of measured values along a time axis and that indicates temporal change in cardiac wall motion, on the basis of the first volume data group and the second volume data group,
generate first correction information and second correction information by correcting the first motion information and the second motion information that are displaying objects such that the first motion information and the second motion information are synchronized with each other on the basis of a cardiac phase, and
generate a motion information image in which the first correction information and the second correction information are arranged along the time axis such that time phases of the first correction information and the second correction information are aligned on the basis of a predetermined cardiac phase; and
a display controlling unit configured to control so that the motion information image is displayed on a predetermined display unit.

2. The ultrasound diagnosis apparatus according to claim 1, wherein
the motion information generating unit is configured to generate a plurality of temporal change curves as the first correction information and the second correction information, and generate the motion information image by arranging a plurality of graphs such that time phases of the temporal change curves are aligned.

3. The ultrasound diagnosis apparatus according to claim 1, wherein
the motion information generating unit is configured to generate a plurality of temporal change curves as the first correction information and the second correction information, and generate the motion information image by superimposing the temporal change curves in one graph.

4. The ultrasound diagnosis apparatus according to claim 1, further comprising:
a calculating unit configured to calculate a temporal difference between an extremum contained in the first correction information and an extremum contained in the second correction information, wherein
the display control unit is configured to control so that the temporal difference calculated by the calculating unit is displayed on the predetermined display unit, in addition to the motion information image.

5. The ultrasound diagnosis apparatus according to claim 1, wherein
the motion information generating unit is configured to set, as an origin, a measured value corresponding to a reference cardiac phase that is set in advance, from among the measured values contained each of the first motion information and the second motion information, thereby aligning start points of the first motion information and the second motion information that are the temporal change information, and interpolate a measured value of one of the first motion information and the second motion information at an elapsed time from the start point of the measured values contained in other one of the first motion information and the second motion information, by using a measured value that is measured near the elapsed time in the one of the first motion information and the second motion information, thereby generating the first correction information and the second correction information.

6. The ultrasound diagnosis apparatus according to claim 1, wherein
the motion information generating unit is configured to relatively adjust durations between reference cardiac phases, between the first motion information and the second motion information that are the temporal change information, and interpolate measured values at a plurality of relative elapsed times that are obtained by dividing the relatively-adjusted duration between the reference cardiac phases by a predetermined interval, by using a measured value that is measured near each of the relative elapsed times in each of the first motion information and the second motion information, thereby generating the first correction information and the second correction information.

7. The ultrasound diagnosis apparatus according to claim 1, wherein
the motion information generating unit is configured to track tracking points that are set on myocardial tissue that is visualized in each volume data, on the basis of a speckle pattern, thereby generating the first motion information and the second motion information.

8. The ultrasound diagnosis apparatus according to claim 1, wherein
the motion information generating unit is configured to generate information related to a volume of at least one of a ventricle and an atrium, as the first motion information and the second motion information.

9. The ultrasound diagnosis apparatus according to claim 1, wherein
the motion information generating unit is configured to generate an overall area change ratio, a temporal change rate of the overall area change ratio, overall strain, an overall strain rate, an overall displacement of myocardial tissue, or a velocity of the overall displacement of the myocardial tissue of at least one of a ventricle and an atrium, as the first motion information and the second motion information.

10. The ultrasound diagnosis apparatus according to claim 1, wherein
the motion information generating unit is configured to generate a regional area change ratio, a temporal change rate of the regional area change ratio, regional strain, a regional strain rate, a regional displacement of myocardial tissue, or a velocity of the regional displacement of the myocardial tissue of at least one of a ventricle and an atrium, as the first motion information and the second motion information.

11. The ultrasound diagnosis apparatus according to claim 1, wherein
the image generating unit is configured to generate a plurality of pairs of volume data, each of which is a pair of the first volume data group and the second volume data group, by performing three-dimensional scanning on a site of a same subject at a plurality of different times,
the motion information generating unit is configured to generate correction information pairs, each of which is formed of the first correction information and the second correction information, for the respective pairs of the volume data, and generates motion information image pairs from the correction information pairs, and
the display controlling unit is configured to control so that the motion information image pairs generated by the motion information generating unit are displayed on the predetermined display unit side by side.

12. The ultrasound diagnosis apparatus according to claim 1, wherein
the motion information generating unit is configured to generate one of the first motion information and the second motion information by taking one of the first volume data group and the second volume data group as a processing object, and
the display controlling unit is configured to control so that one of the first motion information and the second motion information generated by the motion information generating unit is displayed on the predetermined display unit.

13. An image processing apparatus comprising:
a motion information generating unit configured to
generate first motion information on cardiac wall motion of at least one of a left ventricle and a left atrium and second motion information on cardiac wall motion of at least one of a right ventricle and a right atrium, each of the first motion information and the second motion information being temporal change information that is made up of a plurality of measured values along a time axis and that indicates temporal change in cardiac wall motion, on the basis of a first volume data group including a region related to a left side of a heart of a subject and a second volume data group including a region related to a right side of the heart, each of the first volume data group and the second volume data group being obtained from volume data that is generated by three-dimensionally scanning the heart of the subject with an ultrasound wave for a duration of one or more heartbeats,
generate first correction information and second correction information by correcting the first motion information and the second motion information that are displaying objects such that the first motion information and the second motion information are synchronized with each other on the basis of a cardiac phase, and
generate a motion information image in which the first correction information and the second correction information are arranged along the time axis such that time phases of the first correction information and the second correction information are aligned on the basis of a predetermined cardiac phase; and
a display controlling unit configured to control so that the motion information image is displayed on a predetermined display unit.

14. An image processing method comprising:

generating, by a motion information generating unit, first motion information on cardiac wall motion of at least one of a left ventricle and a left atrium and second motion information on cardiac wall motion of at least one of a right ventricle and a right atrium, each of the first motion information and the second motion information being temporal change information that is made up of a plurality of measured values along a time axis and that indicates temporal change in cardiac wall motion, on the basis of a first volume data group including a region related to a left side of a heart of a subject and a second volume data group including a region related to a right side of the heart, each of the first volume data group and the second volume data group being obtained from volume data that is generated by three-dimensionally scanning the heart of the subject with an ultrasound wave for a duration of one or more heartbeats;

generating, by the motion information generating unit, first correction information and second correction information by correcting the first motion information being a displaying object and the second motion information being a displaying object in such a manner that the first motion information and the second motion information are synchronized with each other on the basis of a cardiac phase;

generating, by the motion information generating unit, a motion information image in which the first correction information and the second correction information are arranged along the time axis such that time phases of the first correction information and the second correction information are aligned on the basis of a predetermined cardiac phase; and controlling, by a display controlling unit, so that the motion information image is displayed on a predetermined display unit.

* * * * *